United States Patent
Lowry et al.

(10) Patent No.: US 6,662,941 B2
(45) Date of Patent: Dec. 16, 2003

(54) SHIPPING PACKAGE FOR HAZARDOUS MATERIAL VIALS AND OTHER FRAGILE ITEMS

(75) Inventors: James Lowry, Florence, SC (US); Graeme Stuart Durban Boyd-Moss, Hampshire (GB); Francisco P. Olano, Camden, SC (US)

(73) Assignee: Sonoco Absorbent Technologies, LLC, Hartsville, SC (US)

( * ) Notice: Subject to any disclaimer, the term of this patent is extended or adjusted under 35 U.S.C. 154(b) by 93 days.

(21) Appl. No.: 09/999,402

(22) Filed: Nov. 15, 2001

(65) Prior Publication Data

US 2002/0088723 A1 Jul. 11, 2002

Related U.S. Application Data

(63) Continuation-in-part of application No. 09/758,921, filed on Jan. 11, 2001.

(51) Int. Cl.[7] ............................................. B65D 81/16
(52) U.S. Cl. ....................................... 206/204; 206/366
(58) Field of Search .................................. 206/363, 204, 206/232, 570, 571, 364, 365, 366, 438; 220/495.01, 495.02, 23.9, 23.91

(56) References Cited

U.S. PATENT DOCUMENTS

| | | | | |
|---|---|---|---|---|
| 3,621,994 A | * | 11/1971 | Brown | 206/446 |
| 3,933,302 A | * | 1/1976 | Reid et al. | 426/128 |
| 4,235,341 A | * | 11/1980 | Martin et al. | 206/830 |
| 4,702,385 A | * | 10/1987 | Shillington et al. | 220/481 |
| 4,748,069 A | * | 5/1988 | Cullen | 428/195 |
| 4,872,563 A | * | 10/1989 | Warder et al. | 53/471 |
| 4,927,010 A | * | 5/1990 | Kannankeril | 206/204 |
| 5,042,683 A | | 8/1991 | Shaw et al. | |
| 5,186,900 A | * | 2/1993 | Jensen et al. | 422/104 |
| 5,511,657 A | * | 4/1996 | Gnau et al. | 206/204 |
| 5,560,487 A | * | 10/1996 | Starr | 206/438 |
| 6,145,685 A | | 11/2000 | Dick | |
| 6,345,719 B1 | * | 2/2002 | Jaycox | 206/570 |
| 6,446,794 B1 | * | 9/2002 | Hacikyan | 206/204 |
| 6,523,681 B1 | * | 2/2003 | Hacikyan | 206/204 |

FOREIGN PATENT DOCUMENTS

| | | | |
|---|---|---|---|
| DE | 924 339 C | | 5/1956 |
| DE | 3624410 A1 | * | 1/1988 |
| EP | 0 336 107 A2 | | 10/1989 |
| GB | 304 984 | | 1/1929 |
| WO | WO 01/58764 A2 | | 8/2001 |

* cited by examiner

Primary Examiner—Shian Luong
(74) Attorney, Agent, or Firm—Alston & Bird LLP

(57) ABSTRACT

A shipping package for protecting a fragile item such as a sample vial comprises a crush-resistant inner container comprising a tube formed from spirally wound fibrous plies adhered together, and an outer container surrounding the inner container. The outer container comprises a semi-rigid can formed of fluid-impervious, flexible polymer and having a receptacle portion and a closure portion releasably fastenable to the receptacle portion so as to render the outer container substantially impervious to fluid outside the outer container. The inner container preferably has a liner of absorbent material. The outer container preferably is formed of polyethylene teraphthalate. The receptacle and closure portions of the outer container preferably are threaded so that the closure portion is screwed onto the receptacle portion.

33 Claims, 4 Drawing Sheets

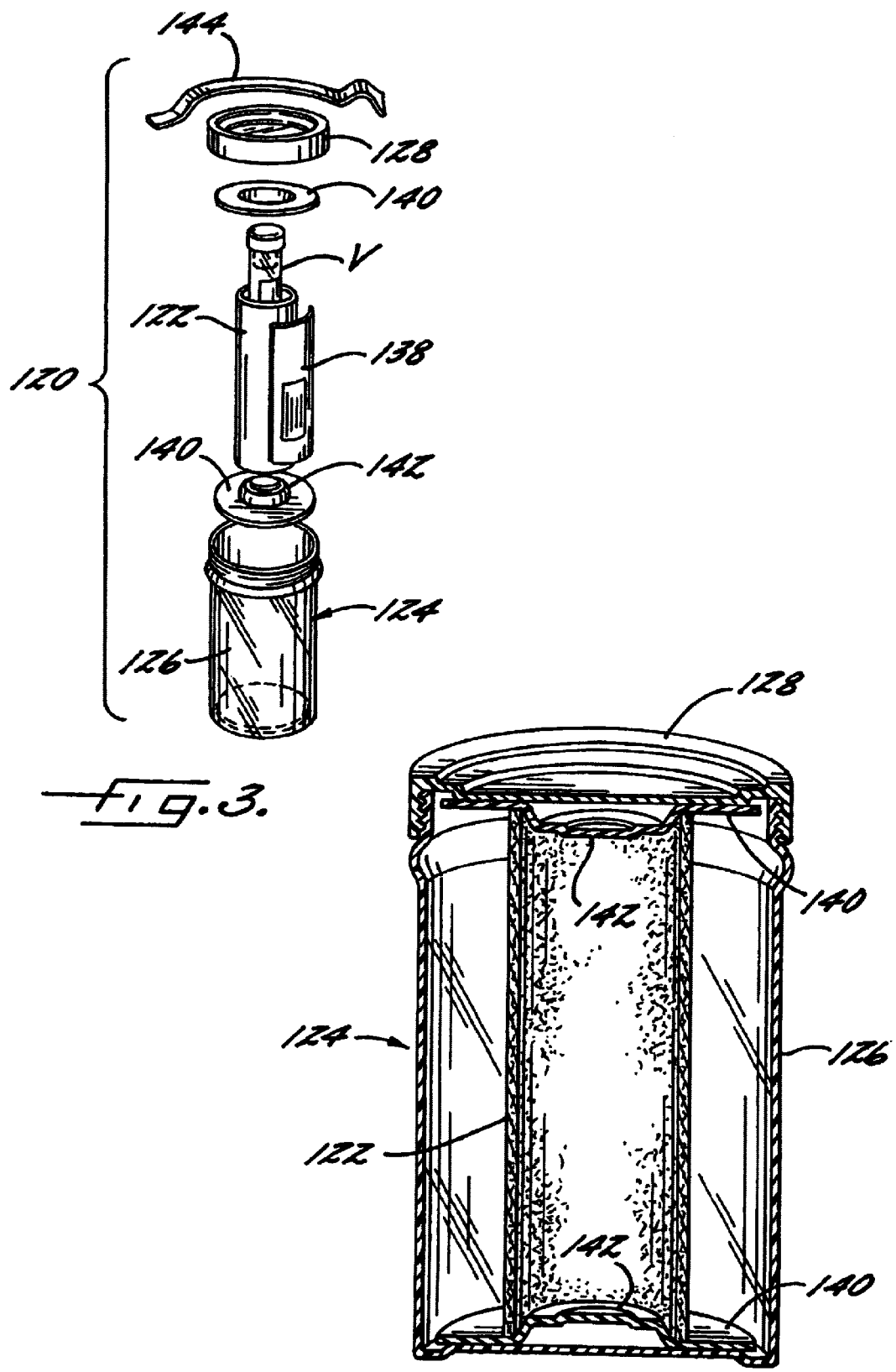

SHIPPING PACKAGE FOR HAZARDOUS MATERIAL VIALS AND OTHER FRAGILE ITEMS

CROSS-REFERENCE TO RELATED APPLICATION

The present application is a continuation-in-part of U.S. patent application Ser. No. 09/758,921 filed Jan. 11, 2001, the entire disclosure of which is incorporated herein by reference.

FIELD OF THE INVENTION

The present invention relates to a shipping or transport package.

BACKGROUND OF THE INVENTION

Transport of hazardous goods, in particular medical samples, is subject to regulations from various regulatory bodies. The International Air Transport Association (IATA), a trade association of the world's airlines, has promulgated regulations for transporting such hazardous goods by air. The IATA regulations prescribe requirements for security against leakage in general, and in particular against crush-induced leakage. There are different levels of regulation for different samples. The more hazardous is the sample, the more severe is the regulation. For example, IATA Transport of Dangerous Goods Regulation 650 prescribes requirements for shipping containers for relatively lower-risk materials that include diagnostic specimens and biological products, whereas Regulation 602 governs the shipping of relatively higher-risk materials such as samples known or reasonably expected to contain infectious microorganisms. Both of these regulations require that a package for shipping medical diagnostic or infectious samples have a water-tight primary container in which the sample is contained and a water-tight secondary container that contains the primary container. The package must have sufficient absorbent between the primary and secondary containers to absorb all liquid contained in the sample. Either the primary container or the secondary container must be able to withstand a pressure differential of 14 psi. Furthermore, the package must withstand a drop from a specified height onto a rigid floor. Packages containing infectious samples must also withstand a 7 kilogram rod dropped onto the package from a height of one meter.

A known medical sample transport package, to meet the severe regulations, includes:
  a closed sample-tube containing the sample;
  an envelope of absorbent material, into which the sample-tube is placed;
  an inner plastics material bottle, which is sealable with the sample-tube and envelope enclosed;
  an outer plastic bottle of heavier construction to provide crush strength; and
  a cardboard box to receive the outer bottle for its dispatch through the mail, which routinely includes air freighting. Such a package is inevitably expensive.

U.S. Pat. No. 5,984,087 (Hacikyan) describes a packaging container comprising an envelope of water-insoluble material having a lining comprising a water-soluble material trapping an absorbent material. In the event of leakage, the water-soluble material dissolves releasing the absorbent material, which can soak up leaked liquid to prevent its release from the envelope. Similar products are disclosed in U.S. Pat. Nos. 4,748,069 and 4,853,266 (both to Cullen). A drawback of the products disclosed in these three patents is that the water-soluble material requires time to dissolve before the water-absorbent material is released, so giving liquid time to migrate and find escape routes. A further drawback is that these packages do not provide significant protection against crush-induced leakage.

International Patent Application WO95/16620 (Noax AB) discloses a package comprising a liquid impermeable layer and an absorbent layer, the absorbent layer possibly comprising super-absorber fibers or powder. Such a package does not provide significant protection against crush-induced leakage.

The parent application to the present application discloses a transport package that achieves substantial resistance to crush-induced leakage as well as meeting various other aspects of the applicable regulations for transporting hazardous samples by air. The package in preferred embodiments includes a substantially rigid tube formed of spirally wound paperboard plies for containing a primary container in the form of a sealed sample tube or vial. An innermost layer of the tube comprises a liner formed of absorbent material. The outermost layer of the tube can be a waterproof material. Removable end caps close the open ends of the spirally wound paperboard tube. With end caps suitably sealed to the tube, the transport package is capable of meeting all applicable regulations. It is a challenge, however, to provide the requisite degree of sealing of the end caps to the tube to meet the requirement of withstanding a 14 psi pressure differential, and to do so with a cost-efficient structure that is also convenient to use.

With the above-noted transport packages, the recipient of the package has no way of determining whether the sample vial contained in the package has leaked, except by opening the package, which may result in the recipient coming into contact with the leaked substance. This is clearly undesirable, particularly in the case of infectious samples. Thus, it would be desirable to be able to determine the condition of the sample while protecting the recipient against contact with any leaked material that may be present inside the package.

SUMMARY OF THE INVENTION

The present invention seeks to provide a shipping package that is convenient to use, and that achieves a substantial resistance to crushing and pressure differential in a relatively simple and cost-efficient manner. The invention in some embodiments also enables a person to visually check the condition inside the package before opening it. In accordance with a first aspect of the invention, a shipping package for protecting a fragile item such as a sample vial comprises a crush-resistant inner container comprising a tube formed from spirally wound fibrous plies adhered together, and an outer container surrounding the inner container. The outer container comprises a semi-rigid can formed of fluid-impervious, flexible polymer and has a receptacle portion and a closure portion releasably fastenable to the receptacle portion so as to render the outer container substantially impervious to fluid outside the outer container. Thus, crush-resistance is provided by the inner container, and resistance to fluid pressure is provided by the outer container. The outer container also can provide resistance to puncture when it is formed of a suitable polymer material and has a sufficient wall thickness.

The inner container can be formed of paperboard plies, and may additionally comprise other non-paperboard layers. Preferably, an innermost layer or liner of the tube is an absorbent material, which may incorporate a super-absorbent polymer.

The outer container preferably is formed of a polyethylene material, most preferably polyethylene teraphthalate. The outer container can be formed by various techniques, preferably by stretch blow molding. In a preferred embodiment of the invention, an open end of the receptacle portion of the outer container is threaded and the closure portion is threaded for releasably screwing onto the open end of the receptacle portion. The threaded engagement between the closure and receptacle portions enables a fluid-tight seal to be accomplished conveniently and cost-efficiently.

Preferably, at least a portion of the outer container is transparent to allow viewing into the interior of the outer container from outside thereof. In a particularly preferred embodiment, an open end of the inner container is adjacent an end wall of the outer container, and at least the end wall of the outer container is transparent to allow viewing into the open end of the inner container from outside the outer container. Accordingly, the condition inside the outer container can be assessed without having to open the outer container; in particular, visible evidence of leakage of a sample vial contained in the inner container may be seen from outside the outer container. The entire receptacle portion of the outer container preferably is transparent; thus, it is possible to view a label or other paperwork stored inside the outer container without having to open the outer container and remove the paperwork. The package preferably has an annular space between the inner and outer containers for storing the paperwork.

In one embodiment of the invention, the inner container is a tube open at both ends, and there are projections formed on the end wall of the receptacle portion and on the closure portion of the outer container that fit inside the open ends of the inner container to fix the inner container in position in the outer container. Alternatively, the projections can be formed on separate disks that are inserted into the receptacle portion of the outer container at opposite ends of the inner container. It is also possible to fix the inner container in the outer container by sizing the outer container to fit closely about the inner container.

A package in accordance with the invention can further comprise a shipping container surrounding the outer container. The shipping container can be a flexible bag or envelope, or a carton, for example.

BRIEF DESCRIPTION OF THE DRAWINGS

The above and other objects, features, and advantages of the invention will become more apparent from the following description of certain preferred embodiments thereof, when taken in conjunction with the accompanying drawings in which:

FIG. 3 is an exploded view of a package in accordance with a second embodiment of the invention;

FIG. 4 is a cross-sectional view of the package of FIG. 3;

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
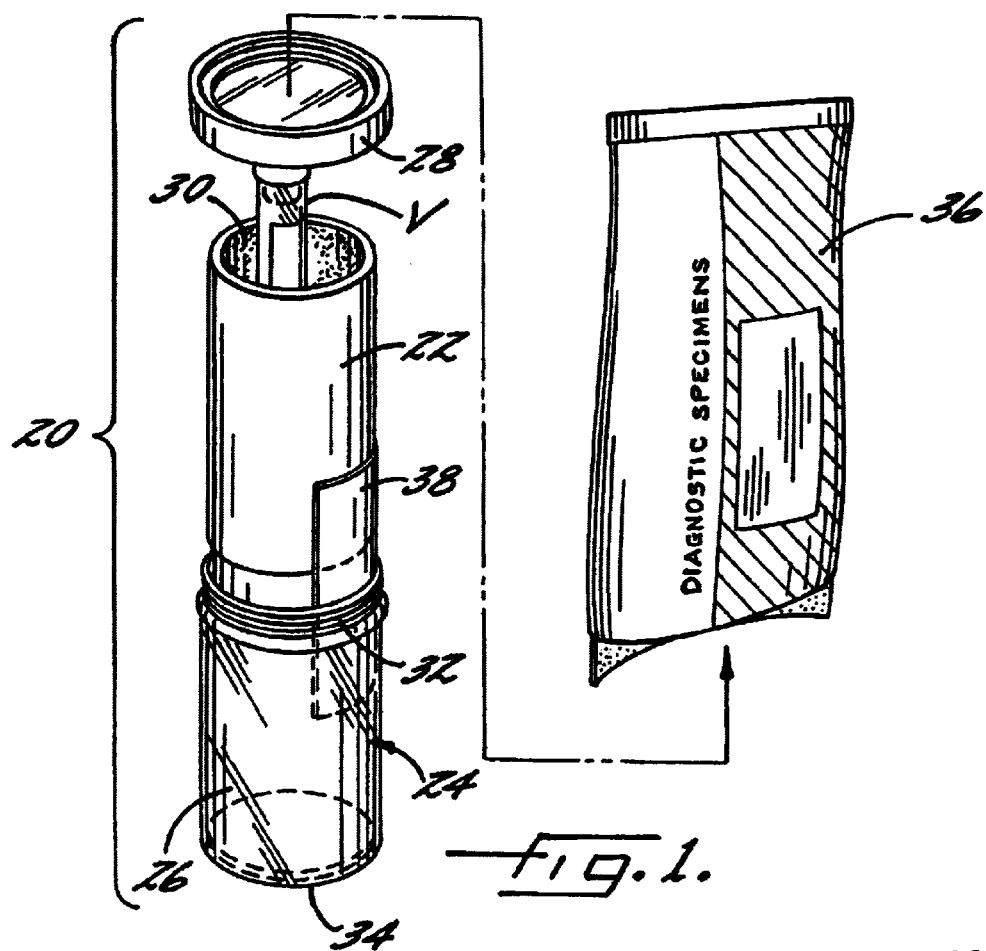
FIG. 1 is an exploded view of a package in accordance with a first embodiment of the invention.
Figure 2:
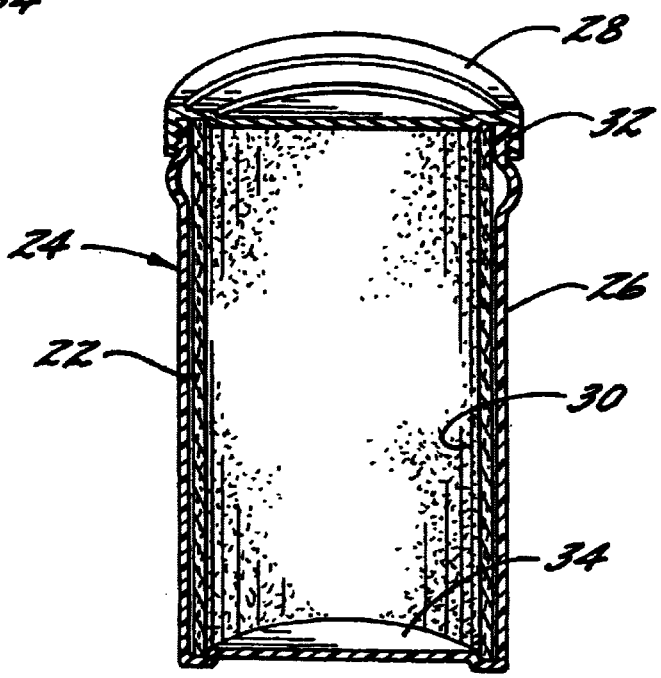
FIG. 2 is a cross-sectional view of the package of FIG. 1.

With reference to FIGS. 1 and 2, a first embodiment of the invention is illustrated. A shipping package 20 comprises a crush-resistant inner container 22 for containing a sample vial V, and a fluid-impervious outer container 24 that surrounds the inner container. The outer container 24 comprises a receptacle portion 26 and a closure portion 28 that releasably fastens to the receptacle portion to seal off the interior of the outer container from the surrounding environment.

The inner container 22 preferably comprises a spirally wound tube as described in parent application Ser. No. 09/758,921. The tube is formed by spirally winding a plurality of plies of fibrous material onto a cylindrical forming mandrel and adhering the plies together with suitable adhesive. The plies preferably comprise paperboard, although non-paperboard plies can also be incorporated. In particular, the innermost layer or lining of the tube 22 preferably comprises an absorbent material 30 capable of absorbing a substantial quantity of liquid in a short amount of time. A ply formed of the absorbent material 30 is the first ply wound onto the forming mandrel, and then a structural ply of paperboard or other strong material is wound onto the absorbent material ply and adhered thereto, followed by additional structural plies, the number of which depends on the desired wall thickness of the tube 22 and the thickness of each of the plies.

The absorbent lining 30 of the tube preferably comprises a web of non-woven carrier, such as polyethylene, having air laid onto it a mixture of cellulose, super-absorbent fiber, and a bi-component fiber as a binder. A discussion of air laid materials can be found at http://www.technica.net/NT/NT2/multifunctionalfibers.htm.

A suitable material for the absorbent lining 30 would be the type of absorbent non-woven material disclosed in WO98/38040, incorporated herein by reference, which comprises a web of 52% wood pulp fiber, 30% super-absorbent fiber, and 18% thermoplastic bonding material, air laid onto a non-woven base tissue (for example, a polyethylene tissue). A suitable super-absorbent fiber is sold under the OASIS trade mark by Technical Absorbents Limited of the United Kingdom (http://www.technical-absorbents.co.uk/). A suitable thermoplastic bonding material is a hydrophilic bi-component fiber comprising polyethylene coated polypropylene sold by Danaklon A/S of Varde, Denmark.

However, such a material has only limited absorbency, and so a higher proportion of super-absorbent fiber can be used. The absorbency and quantity of the lining material 30 used to line the tube 22 should preferably be sufficient to absorb the entire liquid contents of any sample vial V inserted into the tube 22. A preferred composition for the liner 30 comprises approximately 20% bi-component fiber, approximately 55% super-absorbent fiber, and approximately 25% cellulose. This is laid onto the non-woven tissue (for example Licontrol™ available from Jacob Holm industries, Soultz, France). The super-absorbent fiber serves to absorb liquids. The cellulose provides water passage to prevent the super-absorbent fiber blocking the material as it swells on absorbing water. The bi-component fiber bonds the component parts together and provides strength, and the non-woven tissue provides a support for the materials.

A typical formulation would comprise bi-component fiber 25 gsm (grams per square meter), super-absorbent fiber 62 gsm, cellulose 30 gsm, and non-woven tissue 17 gsm.

Such super-absorbent-containing air laid materials are readily obtainable from manufacturers of air laid products, for example Dan-Webforming Research & Development A/S.

The inner container 22 is sized in accordance with the desired capacity of the container. For storing a single medical sample vial having typical maximum dimensions of about 20 mm in diameter and 100 mm in length, the inner container 22 suitably has an inside diameter of about 25–30 mm and a length of about 110 mm. The wall thickness of the inner container 22 is chosen to give the container adequate resistance to crushing. For a given crush load exerted on the container, the wall thickness required to withstand the load without crushing depends on a number of factors, including the diameter of the container and the strength properties of the structural plies making up the container. Thus, it is not possible to give container dimensions that are universally applicable to all situations. As an example, however, an inner container 22 having the above-noted dimensions and formed entirely of paperboard plies as the structural plies can suitably have a wall thickness of about 5 mm.

The outer container 24 is formed of a polymer material. Suitable polymer materials include polyethylene, particularly high-density polyethylene, and most preferably polyethylene teraphthalate (PET). The receptacle portion 26 of the outer container advantageously is formed by stretch blow molding. The receptacle portion comprises a tubular sidewall that is open at one end. The open end of the receptacle portion has an external thread 32 formed thereon. The closure portion 28 has a corresponding internal thread so that the closure portion is releasably fastenable to the receptacle portion by screwing the closure portion onto the threaded open end of the receptacle portion. The opposite end of the receptacle portion is closed by an end wall 34 joined to the tubular sidewall. The threaded engagement between the closure and receptacle portions provides a substantially fluid-tight seal therebetween, such that the interior of the outer container 24 is sealed off from the environment surrounding the outer container.

In the embodiment of FIGS. 1 and 2, the inner diameter of the outer container 24 is only slightly greater than the outer diameter of the inner container 22, such that the outer container fits closely about the inner container. The end wall 34 of the outer container preferably is pushed in toward the interior of the container in a central circular region of the end wall, and the pushed-in region of the end wall fits inside the open end of the inner container 22. Accordingly, if the sample vial V should leak liquid when the package 20 is sitting upright (i.e., supported on the end wall 34), liquid not absorbed by the absorbent liner 30, if any, will tend to collect in the lowest point, which is the region of the end wall 34 adjacent the wall of the inner container 22. At least the end wall 34 of the outer container 24 is transparent. Thus, it is possible to see any such leaked liquid from outside the outer container, without having to open the outer container. It is also possible to see through the transparent end wall 34 into the inside of the inner container, and thus monitor the condition of the sample vial V from outside the package. If there is visible evidence of leakage, the recipient can take special precautions when opening the package to avoid contact with the leaked liquid.

The package 20 in accordance with the first embodiment further comprises an outer shipping bag 36 for containing the assembly of the outer container 24 and inner container 22. The outer shipping bag 36 preferably is formed of a flexible polymer film or other substantially waterproof material. The container assembly is placed into the shipping bag 36 along with paperwork 38. The paperwork 38 may consist of, for example, an itemized list of the contents of the container. The shipping bag 36 containing the container and paperwork is then sealed closed with a suitable adhesive seal or the like.

The inner container 22 preferably is removable from the outer container 24 so that the inner container can be replaced as needed. Accordingly, there is sufficient radial clearance between the inner and outer containers to allow the inner container to be slid out the open end of the outer container. A new inner container 22 can then be slid into the outer container. This may be necessary, for example, if a sample vial stored in the inner container should leak, thus fouling the inner container with liquid contents of the vial.

A shipping container 120 in accordance with a second embodiment of the invention is illustrated in FIGS. 3 and 4. The shipping container 120 comprises a crush-resistant inner container 122 having an absorbent liner 130, and a fluid-impervious outer container 124. The inner diameter of the outer container 124 is substantially greater than the outer diameter of the inner container 122, such that there is an annular space between the containers. To prevent the inner container 122 from moving about within the outer container, the shipping package includes a pair of insert discs 140 that fit onto the opposite open ends of the inner container 122. Each disc includes a central circular portion 142 that projects out of the plane of the disc toward the opposite disc. The projecting portions 142 fit inside the open ends of the inner container 122, and thereby prevent the inner container from moving radially relative to the discs. The discs thus fix the inner container in a substantially centered position inside the outer container 124. The assembly of the inner container 122 and discs 140 comprises a removable insert assembly that can be removed from the outer container 124 and replaced with a new assembly as needed.

The entire receptacle portion 126 of the outer container 124 is transparent. A label or other paperwork 138 can be inserted into the annular space between the outer and inner containers, and can be viewed through the transparent wall of the outer container from outside thereof.

In use, one end of the inner container 122 is fitted onto one of the discs 140, and the assembly is inserted into the outer container 124. A sealed sample vial V is inserted into the inner container. A label 138, such as an itemized list of the contents of the inner container, is inserted into the space between the inner and outer containers. The other disc 140 is then fitted onto the open end of the inner container. The closure portion 128 is screwed onto the open threaded end of the outer container 124. A tamper-evident tape 144 is then adhered over the closure portion 128 and to the sidewalls of the outer container.

Figure 5:
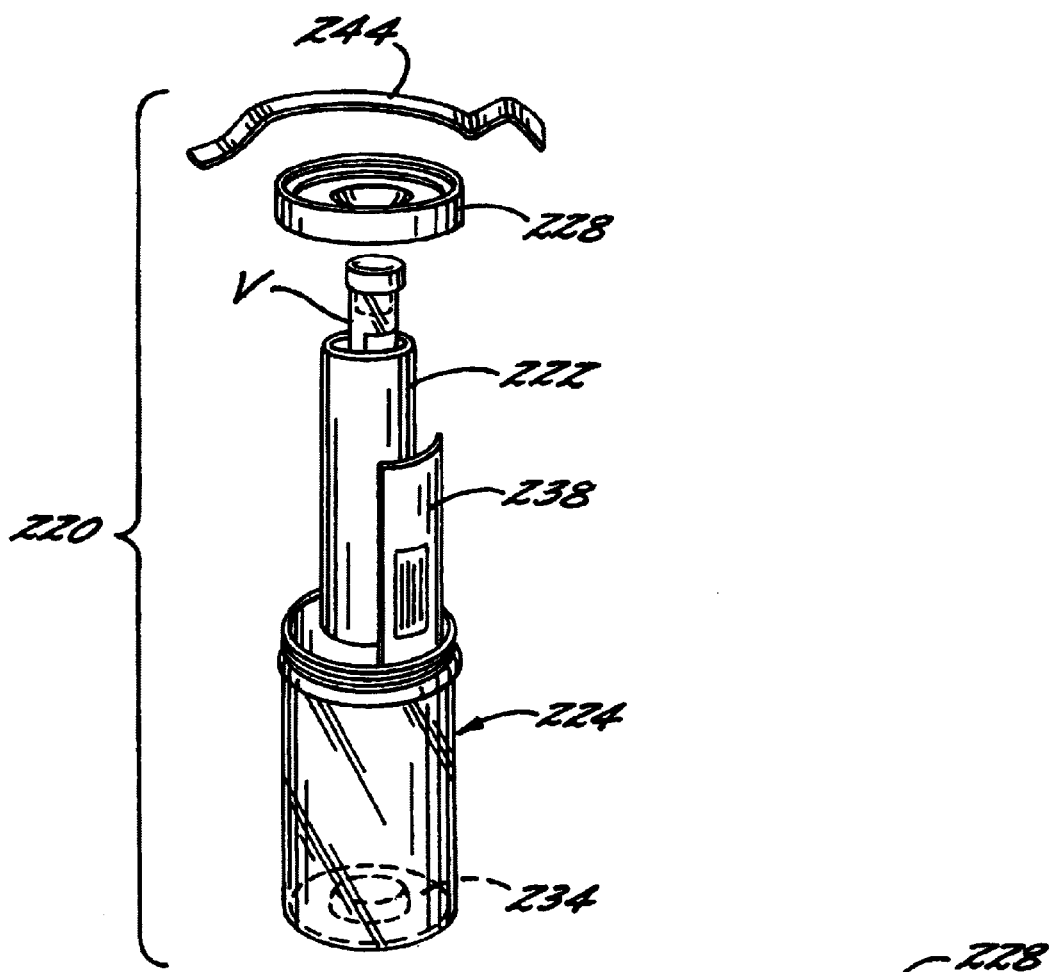
FIG. 5 is an exploded view of a package in accordance with a third embodiment of the invention.
Figure 6:
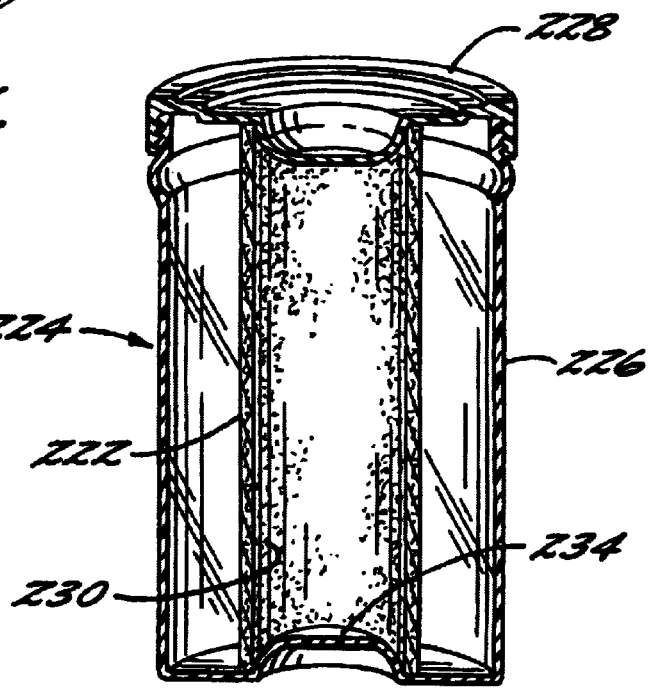
FIG. 6 is a cross-sectional view of the package of FIG. 5.

FIGS. 5 and 6 depict a container 220 in accordance with a third embodiment of the invention. The container 220 comprises an inner container 222 having an absorbent liner 230, and an outer container 224. The container 220 is generally similar to the container 120 of FIGS. 3 and 4, except that the separate discs 140 have been eliminated. Instead, the projecting portions that fit into the open ends of the inner container 222 are formed on the end wall 234 of the outer container and on the closure portion 228 of the outer container. The package 220 also differs in that the inside of the inner container 222 can be viewed through the transparent end wall 234 of the outer container, since there is no disc to obscure the view.

Figure 7:
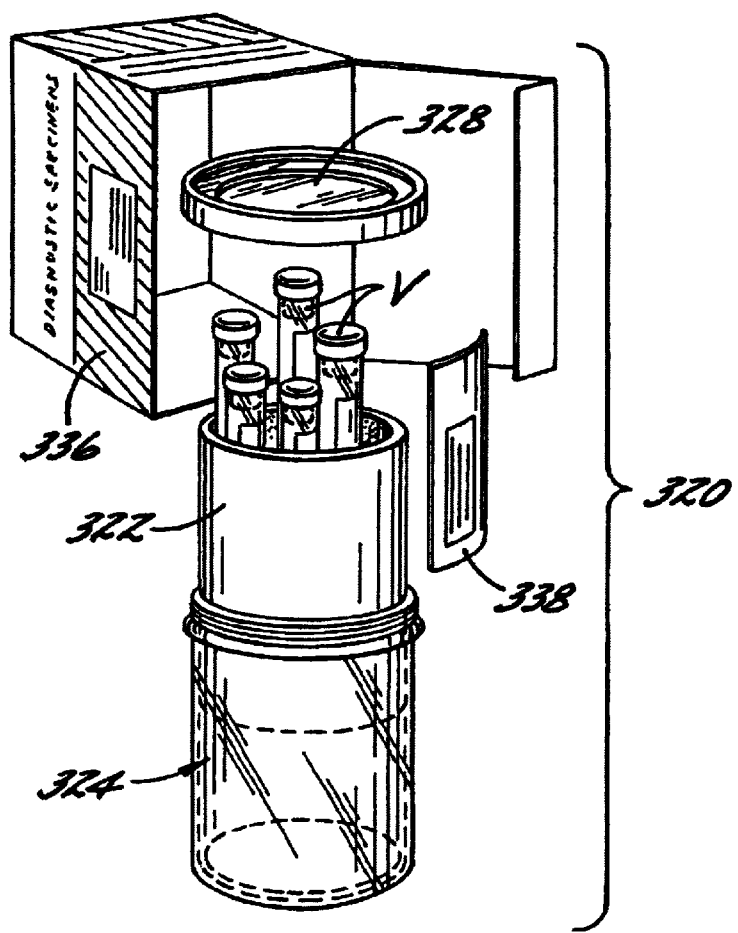
FIG. 7 is an exploded view of a package in accordance with a fourth embodiment of the invention.
Figure 8:
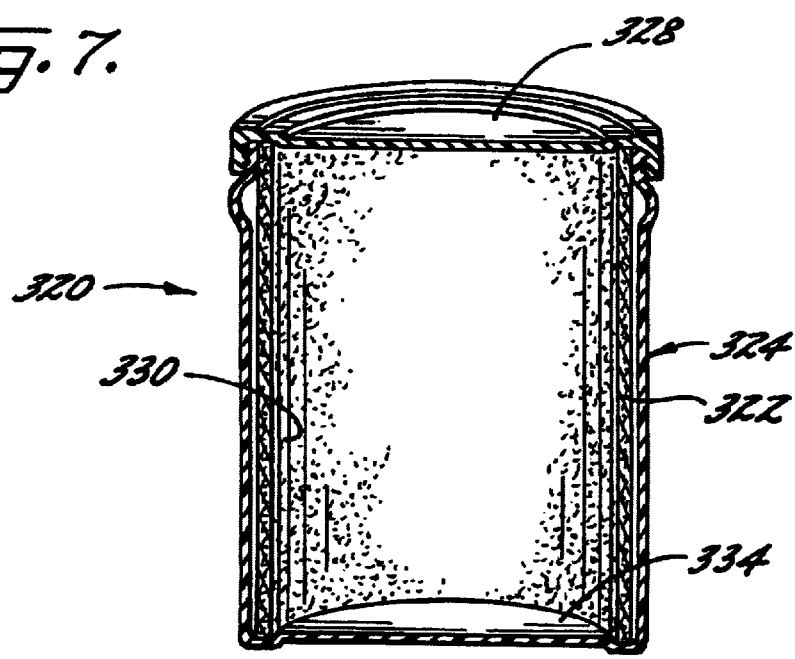
FIG. 8 is a cross-sectional view of the package of FIG. 7.

A package 320 in accordance with a fourth embodiment of the invention is depicted in FIGS. 7 and 8. The package 320 is generally similar in construction to the package 20 shown in FIGS. 1 and 2, except that the assembly of the inner container 322 and outer container 324 is of larger diameter for containing multiple sample vials V. Additionally, the package includes an outer shipping carton 336 rather than a flexible shipping bag.

From the foregoing, it will be appreciated that the present invention provides a shipping package for hazardous sample vials or other fragile items that is simple to use and relatively inexpensive to produce. The sample vial is protected from crushing loads by the inner container. In the illustrated embodiments, the inner container is constructed as a spirally wound tube. However, it is possible within the scope of the invention to form the inner container in other ways. For example, the inner container could be a molded plastic tube of sufficient rigidity to resist crushing. The outer container provides further protection against external loads, and in particular protects the sample vial from external fluid pressure and prevents infiltration of water into the container. The outer container also provides protection against punctures.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A package for protecting a fragile item, comprising:
  a crush-resistant inner container comprising a tube formed from spirally wound fibrous plies adhered together, wherein the inner container has an innermost liner attached thereto and forming an innermost surface of the package adjacent a contained fragile item, the liner comprising absorbent material for absorbing liquid that leaks from the fragile item before the liquid can escape the inner container; and
  an outer container surrounding the inner container, the outer container comprising a semi-rigid can formed of fluid-impervious, flexible polymer and having a receptacle portion and a closure portion releasably fastenable to the receptacle portion so as to render the outer container substantially impervious to fluid outside the outer container.

2. The package of claim 1, wherein the outer container is formed of polyethylene.

3. The package of claim 1, wherein the outer container is formed of polyethylene teraphthalate.

4. The package of claim 1, wherein an open end of the receptacle portion of the outer container is threaded and the closure portion is threaded for releasably screwing onto the open end of the receptacle portion.

5. The package of claim 1, wherein at least a portion of the outer container is transparent to allow viewing into the interior of the outer container from outside thereof.

6. The package of claim 1, wherein an open end of the inner container is adjacent an end wall of the outer container, and at least the end wall of the outer container is transparent to allow viewing into the open end of the inner container from outside the outer container.

7. The package of claim 1, wherein the liner includes super-absorbent polymer.

8. The package of claim 7, wherein the liner comprises a non-woven fibrous layer incorporating the super-absorbent polymer.

9. The package of claim 1, further comprising a shipping container for containing the outer container.

10. The package of claim 9, wherein the shipping container comprises a flexible bag.

11. The package of claim 9, wherein the shipping container comprises a carton.

12. A package for protecting a vial of hazardous material, comprising:
  a crush-resistant inner container configured to store the vial therein, the inner container having an absorbent material attached to and covering an inner surface thereof and forming an innermost surface of the package adjacent a contained vial, the absorbent material thus being positioned to absorb liquid that leaks from the vial before the liquid can escape the inner container; and
  an outer container surrounding the inner container, the outer container comprising a semi-rigid can formed of fluid-impervious, flexible polymer and having a receptacle portion and a closure portion releasably fastenable to the receptacle portion so as to render the outer container substantially impervious to fluid outside the outer container.

13. The package of claim 12, wherein at least a portion of the outer container is transparent to allow viewing of the inner container without opening the outer container.

14. The package of claim 12, wherein the receptacle and closure portions of the outer container are formed of a transparent material.

15. The package of claim 12, wherein the receptacle and closure portions of the outer container are formed of a polymer material.

16. The package of claim 12, wherein the outer container is formed of polyethylene.

17. The package of claim 12, wherein the outer container is formed of polyethylene teraphthalate.

18. The package of claim 12, wherein an open end of the receptacle portion is threaded, and the closure portion comprises a threaded cap that is screwed onto the threaded open end of the receptacle portion.

19. The package of claim 12, wherein the inner container comprises a spirally wound tube formed of fibrous plies.

20. The package of claim 19, wherein the innermost layer of absorbent material is spirally wound.

21. The package of claim 20, wherein the absorbent material comprises a super-absorbent polymer.

22. The package of claim 12, wherein the receptacle and closure portions of the outer container are threaded to allow the closure portion to be removably screwed onto the receptacle portion.

23. The package of claim 22, wherein there is a space between an outer surface of the inner container and an inner surface of the receptacle portion of the outer container such that paperwork can be inserted into said space.

24. The package of claim 23, wherein the outer container is transparent to allow viewing of paperwork in said space without opening the outer container.

25. The package of claim 12, wherein the inner container is removable from the outer container and replaceable with a new inner container.

26. A package for protecting a vial of hazardous material, comprising:
- a crush-resistant inner container configured to store the vial therein, the inner container having an absorbent material covering an inner surface thereof; and
- an outer container surrounding the inner container, the outer container comprising a semi-rigid can formed of fluid-impervious, flexible polymer and having a receptacle portion and a closure portion releasably fastenable to the receptacle portion so as to render the outer container substantially impervious to fluid outside the outer container;
- wherein the receptacle portion has a generally tubular side wall encircling an axis and an end wall generally perpendicular to said axis, and the end wall has a portion that engages one end of the inner container to fix the inner container in position within the receptacle portion.

27. The package of claim 26, wherein the portion engaging the inner container comprises a part of the end wall that is formed to project toward the interior of the outer container.

28. The package of claim 27, wherein the inner container is tubular and open at the one end thereof, and the part of the end wall that projects toward the interior of the outer container is engaged inside the open end of the inner container.

29. The package of claim 12, wherein the inner container is tubular and open at both ends, the outer container receptacle portion has a tubular side wall encircling an axis and having one open end and an opposite end closed by an end wall generally perpendicular to said axis, and the inner container is disposed in the outer container with one end of the inner container opposing the end wall and the other end of the inner container facing the open end of the outer container.

30. The package of claim 29, wherein at least the end wall of the outer container receptacle portion is transparent to allow viewing into the one end of the inner container from outside the outer container.

31. A package for protecting a vial of hazardous material, comprising:
- a crush-resistant inner container configured to store the vial therein, the inner container having an absorbent material covering an inner surface thereof; and
- an outer container surrounding the inner container, the outer container comprising a semi-rigid can formed of fluid-impervious, flexible polymer and having a receptacle portion and a closure portion releasably fastenable to the receptacle portion so as to render the outer container substantially impervious to fluid outside the outer container;
- wherein the inner container is fixed in place in the outer container by a pair of removable disks having projections that engage open ends of the inner container.

32. A package for protecting a vial of hazardous material, comprising:
- a crush-resistant inner container configured to store the vial therein, the inner container having an absorbent material covering an inner surface thereof and forming an innermost surface of the package adjacent a contained vial, the absorbent material thus being positioned to absorb liqiuid that leaks from the vial before the liquid can escape the inner container; and
- an outer container surrounding the inner container, the outer container comprising a semi-rigid can formed of fluid-impervious polymer and having a receptacle portion and a closure portion releasably fastenable to the receptacle portion so as to render the outer container substantially impervious to fluid outside the outer container, the receptacle portion having an end wall adjacent one end of the inner container, at least the end wall of the outer container being transparent to allow the interior of the outer container to be seen from outside thereof.

33. The package of claim 32, wherein the outer container is formed of polyethylene teraphthalate.

* * * * *